(12) United States Patent
Li

(10) Patent No.: US 7,483,127 B1
(45) Date of Patent: Jan. 27, 2009

(54) METHOD AND APPARATUS FOR GENERATING AN IMAGE OF BIOMOLECULAR SENSOR TARGET AREA

(75) Inventor: Peter Y. Li, Andover, MA (US)

(73) Assignee: SRU Biosystems, Inc., Woburn, MA (US)

( * ) Notice: Subject to any disclaimer, the term of this patent is extended or adjusted under 35 U.S.C. 154(b) by 429 days.

(21) Appl. No.: 11/199,873

(22) Filed: Aug. 8, 2005

(51) Int. Cl.
*G01N 21/00* (2006.01)

(52) U.S. Cl. .............. 356/237.1; 356/237.4; 356/237.5

(58) Field of Classification Search ... 356/237.1–237.6, 356/432–448, 364–370, 244–246; 385/12; 422/82.05
See application file for complete search history.

(56) References Cited

U.S. PATENT DOCUMENTS

| | | | |
|---|---|---|---|
| 5,991,048 A * | 11/1999 | Karlson et al. .............. 356/445 |
| 5,999,262 A | 12/1999 | Dobschal et al. ............ 356/358 |
| 6,100,991 A | 8/2000 | Challener ................... 356/445 |
| 6,909,104 B1 * | 6/2005 | Koops et al. ............. 250/493.1 |
| 2002/0127565 A1 | 9/2002 | Cunningham et al. .......... 435/6 |
| 2003/0017581 A1 | 1/2003 | Li et al. .................... 435/287.2 |
| 2003/0027327 A1 | 2/2003 | Cunningham et al. .... 435/287.2 |
| 2003/0027328 A1 | 2/2003 | Cunningham et al. .... 435/287.2 |
| 2003/0059855 A1 | 3/2003 | Cunningham et al. ........ 435/7.9 |
| 2004/0223881 A1 | 11/2004 | Cunningham et al. .... 422/82.05 |
| 2006/0193550 A1 | 8/2006 | Wawro et al. ................. 385/12 |

OTHER PUBLICATIONS

Cunningham et al., "Colorimetric resonant reflection as a direct biochemical assay technique", Sensors and Actuators B 4120, pp. 1-13 (2001).
Cunningham et al., "A plastic colorimetric resonant optical biosensor for multiparallel detection of label-free biochemical interactions", Sensors and Actuators B 4283, pp. 1-8 (2002).
Cunningham et al., "Enhancing the surface sensitivity of colorimetric resonant optical biosensors", Sensors and Actuators B 6779, pp. 1-6 (2002).
Li et al., "A new method for label-free imaging of biomolecular interactions", Sensors and Actuators Bxxx, pp. 1-13 (2003).
International Preliminary Report on Patentability in PCT/US2006/022820, issued Feb. 21, 2008.
PCT International Search Report and Written Opinion of the International Searching Authority for PCT application of SRU Biosystems, Inc., PCT/US2006/022820 dated Nov. 11, 2006.

* cited by examiner

*Primary Examiner*—Tri T. Ton
(74) *Attorney, Agent, or Firm*—McDonnell Boehnen Hulbert & Berghoff LLP

(57) ABSTRACT

Method and apparatus for imaging a target area. Apparatus comprises an adjustable light emitting device that provides a light beam with a user defined spectrum. A filter mechanism receives the light beam and directs the light beam towards a target area. A light collection device collects an amount of light reflected from a target area and generates an image from the reflected light.

7 Claims, 4 Drawing Sheets

FIGURES 3 (a – e)

FIGURES 4 (a – d)
Figure 4(a)
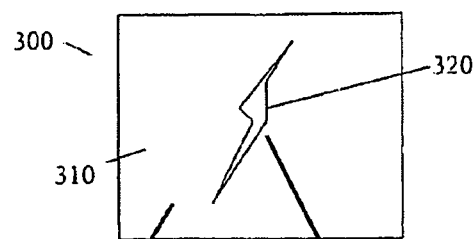
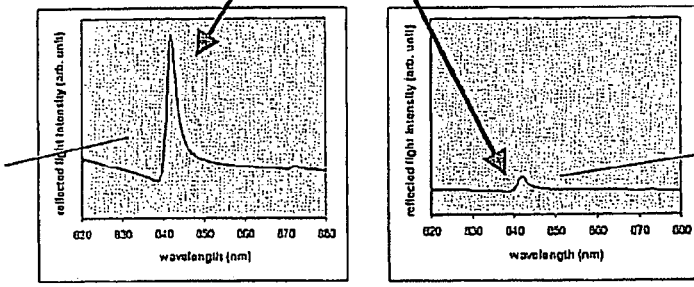
Figure 4(b)
Figure 4(c)
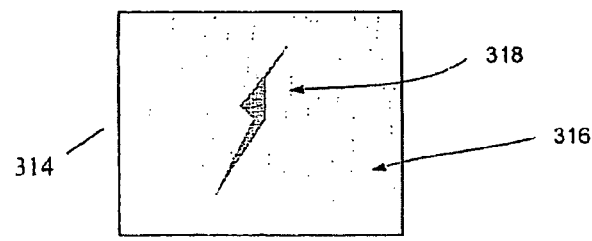
Figure 4(d)

METHOD AND APPARATUS FOR GENERATING AN IMAGE OF BIOMOLECULAR SENSOR TARGET AREA

RELATED APPLICATIONS

This application is related to U.S. provisional application 60/244,312 filed Oct. 30, 2000; U.S. provisional application 60/283,314 filed Apr. 12, 2001; U.S. provisional application 60/303,028 filed Jul. 3, 2001; U.S. patent application Ser. No. 09/930,352 filed Aug. 15, 2001, U.S. patent application Ser. No. 10/059,060 filed Jan. 28, 2002, and U.S. patent application Ser. No. 10/058,626 filed Jan. 28, 2002, all of which are herein entirely incorporated by reference and to which the reader is directed for further information.

BACKGROUND

The invention generally relates to methods, instrumentation and/or devices for interactive generation of an image target area, preferably a biomolecular sensor target area. More specifically, aspects of the present invention are generally directed to an apparatus and method for imaging a target area of a subwavelength structured surface biosensor. Such a biosensor may or may not comprise biomolecular interaction assays. Aspects of the present invention may also be used in the manufacturing, fabrication, inspection, quality control, and/or monitoring of biosensors, such as subwavelength structured surface biosensors. Aspects of the present invention may be applicable in monitoring various biosensor characteristics. For example, uniformity of sensor coatings such as various polymers, or other similar active biochemical active groups may be monitored or investigated.

Applicants' related pending patent applications hereinbefore entirely incorporated by reference disclose various methods and apparatus for the detection of Peak Wavelength Values ("PWVs") of colorimetric resonant optical biosensors. Colorimetric resonant optical biosensors allow biochemical interactions to be analyzed and/or measured on a sensor's surface without using fluorescent tags or colorimetric labels. As disclosed in greater detail in the above incorporated by reference related patent applications, a sensor surface contains an optical structure that, when illuminated with collimated white light, reflects only a narrow band of wavelengths of an applied spectral of light. The narrow wavelength may be described as a spectral "peak." The "Peak Wavelength Value" ("PWV"), namely, the central wavelength of the peak, can change when biological material is deposited and/or removed from the sensor surface. The PWV may also vary if the sensor surface has a blemish or if the sensor surface has a surface inconsistency such as a manufacturing or fabrication fault.

Generally, the instruments collect or gather light reflected from the entirety of the illuminated biosensor surface. In one scenario, the instrument gathers reflected light from multiple locations along the biosensor surface simultaneously. In one arrangement, instrumentation could include a plurality of illumination probes that direct light to a discrete number of positions across the biosensor surface. This instrumentation measures the PWVs of separate locations within the biosensor-embedded microtiter plate using a spectrometer.

As generally described in Applicant's related and co-pending patent applications herein previously incorporated entirely by reference, a guided mode resonant filter (GMRF) based biosensor may be designed to create an optical resonant reflection at a particular narrow band of wavelengths when illuminated with a broadband light source such as white light. When biological material adsorbs to the surface of the GMRF structure, the wavelength of reflected light is modified, and tracked by an instrument that is capable of measuring the PWV of the resonance. The GMRF biosensor contains a diffractive grating structure with discontinuous regions of alternating high and low refractive index, where the period of the diffractive element and the dimensions of the discontinuous regions are significantly lower than the resonant wavelength.

As discussed in the various patent applications incorporated by reference above, Applicants' various previously disclosed systems have numerous advantages. Although the previously discussed systems have numerous advantages, such previously disclosed systems may not be ideal for all types of imaging applications. For example, there may be certain applications or certain imaging situations that require a less complex imaging analysis, result or imaging conclusion. In addition, there may be situations that require a relatively quick result albeit a result that may or may not require a highly accurate imaging conclusion. In addition, such previously disclosed systems can be quite complex and therefore can be generally costly to purchase, operate and/or maintain.

Another limitation of such previously disclosed measuring systems is the amount of time that such systems generally require for image acquisition such as acquiring images at high spatial resolution. For example, such image acquisition at high spatial resolution oftentimes takes on the order of a few minutes per image. There is, therefore, a general need for an imaging system that is more cost efficient. There is also a general need for an imaging system that can generate an acceptable image of acceptable spatial resolution in a more timely manner. There is also a general need for an imaging system that utilizes intervention (such as user intervention) to obtain an acceptable image.

SUMMARY

In one exemplary embodiment, an apparatus for imaging a target area is provided. The apparatus comprises an adjustable light emitting device that provides a light beam having a pre-defined light spectrum. A filtering mechanism directs the light beam towards a target area. A light collection device collects an amount of light reflected from the target area and generates a target area image.

In another exemplary embodiment, an apparatus for generating a biosensor image is provided. The apparatus comprises a light source and an adjustable monochromator optically coupled to the light source. The monochromator adjusts a spectrum of light to a define a narrow band of wavelengths that illuminate a surface of a biosensor target area. A telecentric lens receives a narrow band of wavelengths reflected from the biosensor target area and generates an image of the target area.

In yet another exemplary embodiment of the present invention, an interactive method for imaging a target area is provided. The method comprises the steps of generating a spectrum of light by a light source and receiving the spectrum of light by a monochromator coupled to the light source. The monochromator passes a user defined range of the light spectrum. The monochromator is adjusted such that the defined range of the spectrum of light is centered at a peak wavelength value of the target area. The method further comprises the steps of reflecting at least a portion of the user defined range of said spectrum of light from the target area and receiving the at least a portion of the user defined range of the spectrum of light by a telecentric lens. The telecentric lens utilizes the reflected light to process an image of the target area.

These as well as other advantages of various aspects of the presently disclosed embodiments will become apparent to those of ordinary skill in the art by reading the following detailed description, with appropriate reference to the accompanying figures.

BRIEF DESCRIPTION OF DRAWINGS

Exemplary embodiments are described herein with reference to the drawings, in which:

FIGS. 4(a-d) illustrate various diagrams illustrating certain principles of operation of one embodiment of the system illustrated in FIG. 2.

DETAILED DESCRIPTION

As generally described in Applicant's related and co-pending patent applications hereinbefore entirely incorporated by reference and to which the reader is directed for further information, a guided mode resonant filter (GMRF) based biosensor may be designed to create a sharp optical resonant reflection at a particular narrow band of wavelengths when illuminated with a broadband light source such as white light. When biological material adsorbs to the surface of the GMRF structure, the wavelength of reflected light is modified, and tracked by an instrument that is capable of measuring the peak wavelength value (PWV) of the resonance. The GMRF biosensor contains a diffractive grating structure with discontinuous regions of alternating high and low refractive index, where the period of the diffractive element and the dimensions of the discontinuous regions are significantly lower than the resonant wavelength.

Figure 1:
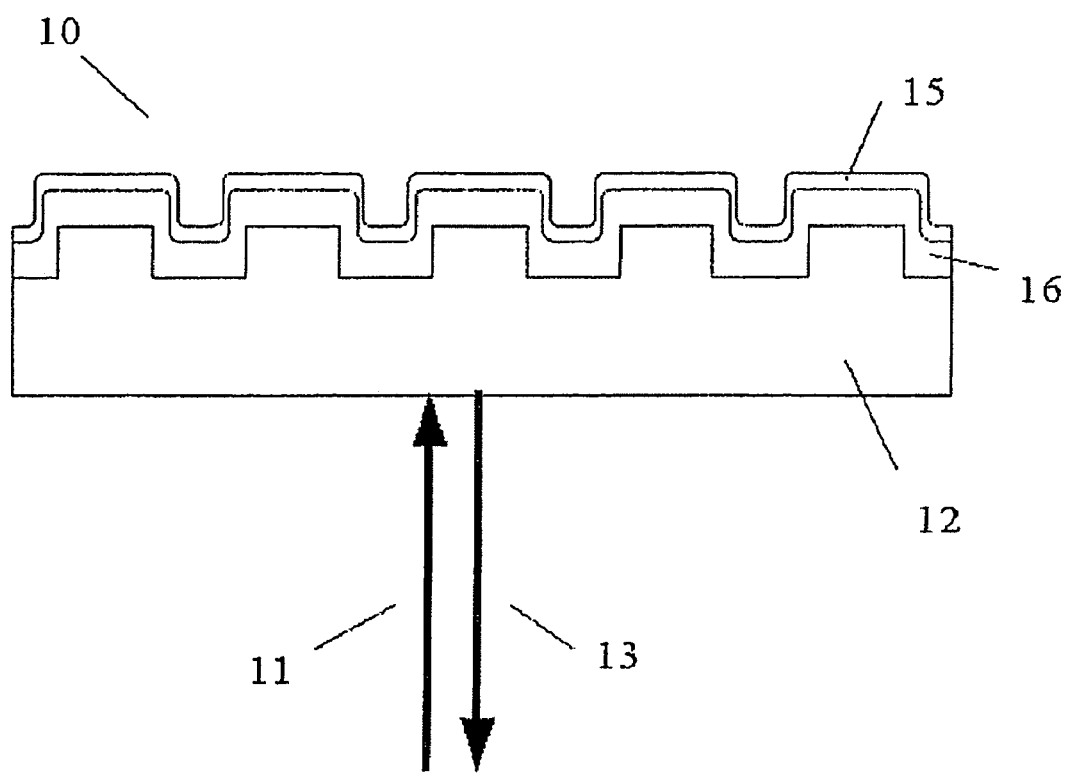
FIG. 1 illustrates a schematic diagram of an embodiment of an optical grating structure.

The currently disclosed apparatus and method is generally directed to interactively generating an image of a specific target area, such specific target area could comprise a biomolecular sensor target area. Such an apparatus and method may be utilized with various types of biosensors. For example, in one arrangement, the disclosed apparatus and method may be used for imaging a target area of a GMRF biosensor. One such GMRF biosensor structure 10 is illustrated in FIG. 1. The biosensor comprises a substrate 12, a high refractive index dielectric material 16, and a surface treatment layer 15. Preferably, the refractive index of the dielectric material layer 16 is higher than that of the substrate 12. For example, the dielectric material may be titanium oxide, with a refractive index of approximately 2.2, while the substrate material may be a polymeric material, with a refractive index of approximately 1.5. The period and shape of the grating structure and the thickness of all layers are designed to generate the guided mode resonance effect at a desired wavelength.

In FIG. 1, incident light 11 is directed toward the biosensor 10 at normal incidence. The reflected light 13 points away from the biosensor, opposite to the incident light 11. Suitable biosensor designs are disclosed in Applicant's previously incorporated patent applications and the articles entitled "Li, P. et al., "A New Method for Label-free Imaging of Biomolecular Interactions," Sensors and Actuators B 99, pp. 6-13 (2004); Cunningham, B. et al., "A Plastic Colormetric Resonant Optical Biosensor for Multiparallel Detection of Label-Free Biochemical Interactions," Sensors and Actuators B 85; pp 219-226 (2002); Cunningham, B. et al., "Enhancing the Surface Sensitivity of Colorimetric Resonant Optical Biosensors," Sensors ands Actuators B 87, pp. 365-370 (2002); and Cunningham, B. et al., "Colorimetric Resonant Reflection as a Direct Biochemical Assay Technique," Sensors and Actuators B 81; pp. 316-328 (2002); herein entirely incorporated by reference and to which the reader is directed for further information. As disclosed in these related patent applications and references, a sharp optical resonant reflection is produced at a particular narrow band of wavelengths when illuminated with a broadband light source such as white light.

Figure 2:
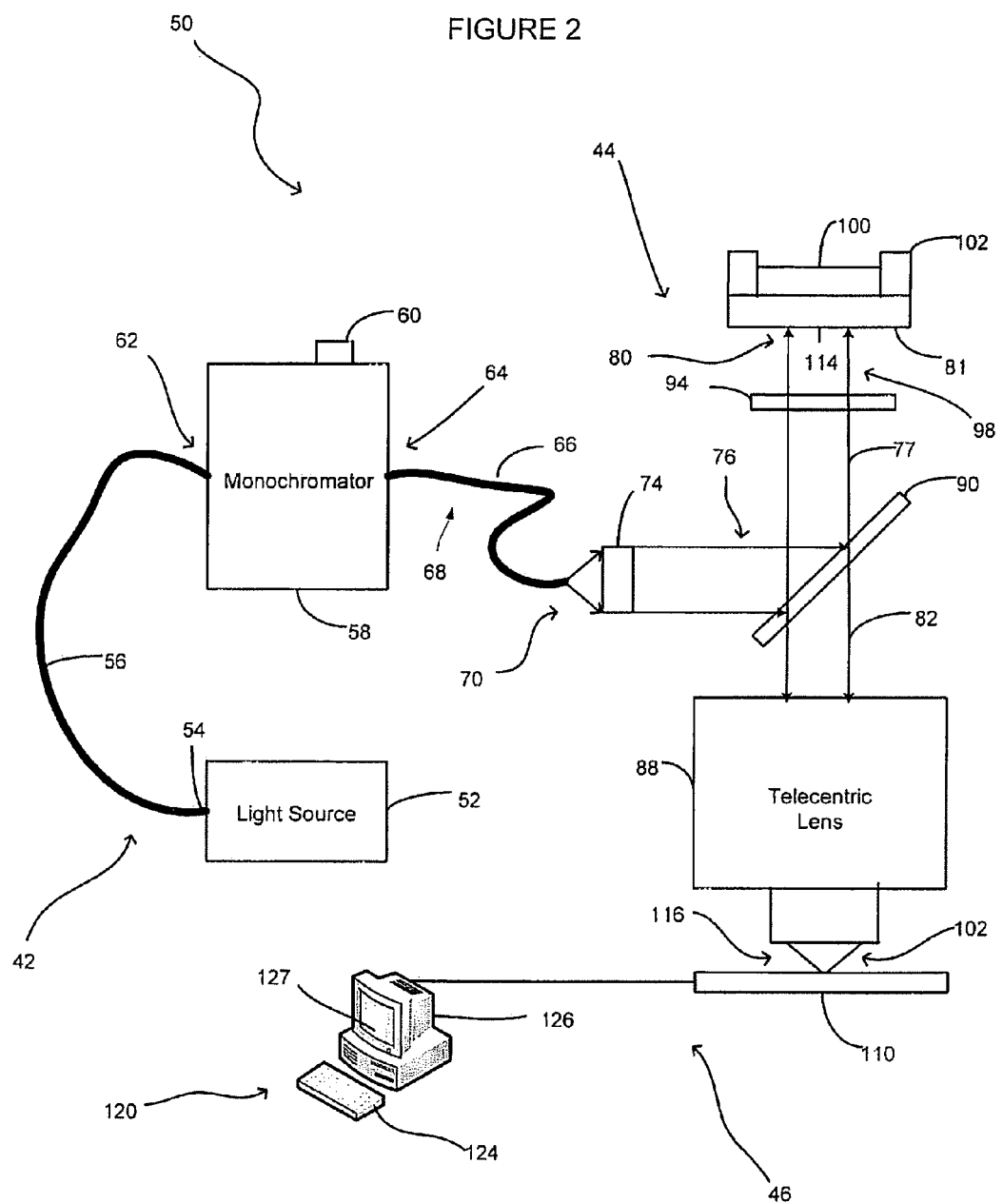
FIG. 2 illustrates a schematic drawing of a first embodiment incorporating aspects of the present invention.

FIG. 2 illustrates a schematic diagram of an imaging system 50. Imaging system 50 incorporates one interactive arrangement for imaging a target area of a biosensor, such as the biosensor illustrated in FIG. 1. Generally, the imaging system 50 comprises an adjustable light emitting device 42, a filtering mechanism 44, and a light collection device 46. The imaging system 50 is used to generate an image of a target area 114 of biosensor 80.

Adjustable Light Emitting Device

In one arrangement, the adjustable light emitting device 42 emits a light beam 76 having a generally user defined wavelength and spectral width. Light beam 76 is transmitted to the filtering mechanism 44. This transmitted light is then processed and is re-directed towards a target area 114 of sensor 80. As illustrated in the arrangement of FIG. 2, the adjustable light emitting device 42 comprises a light source 52 optically coupled to a monochromator 58. Adjustable light emitting device 42 may be utilized to emit light of a certain user defined wavelength and spectral width.

Preferably, this defined wavelength and spectral width is adjusted to generally match or correlate a reflectivity peak for sensor target area 114. In this manner, various different regions or sensor target areas may be investigated and/or evaluated. For example, and as more clearly described below, the light emitting device 42 may be adjusted (e.g., manually, automatically, electronically, or otherwise) to produce an output of varying wavelength and spectral width. It is this light beam 76 with defined wavelength and spectral width that generates a specific reflectivity peak of a sensor target area.

Filtering Mechanism

Filtering mechanism 44 receives light beam 76 from adjustable light emitting device 42, and processes certain aspects of this light beam. In one preferred arrangement, the filtering mechanism 44 initially processes and directs this light towards a surface 81 of a target area 114 of sensor 80. A portion of this processed light is reflected off of sensor surface 81 and is reflected towards a light collection device 46. In one preferred arrangement, the filter mechanism comprises a beam splitter 90 and a polarizer 94.

Light Collection Device

Light collection device 46 receives the reflected light from the filtering mechanism 44 and processes reflected light to generate a sensor image, preferably an image of sensor target area 114. In one preferred arrangement, light collection device 46 comprises a telecentric lens assembly 88 and a CCD camera 110. An image capture system 120, which may or may not include a video monitor 126, may be used for image storage, image manipulation, and/or light spectral adjustment. For example, in one arrangement, the image capture system 120 may be used to provide interactive feedback to the adjustable light emitting device 42.

The imaging system 50 may be used to analyze various types of devices such as sensors, chemical sensors, dry biosensors, or wet biosensors. For example, such biosensors could include biosensors containing liquid containers. In the arrangement illustrated in FIG. 2, the biosensor comprises a liquid container 102. Preferably, the liquid container 102 includes certain sample reagents 100.

Returning to the adjustable light emitting device illustrated in FIG. 2, optical fibers 56 and 66 are used to transmit light between the various components. For example, optical fiber 56 is coupled to an output port 54 of light source 52 and transmits light generated by light source 52 to an input port 62 of monochromator 58. Optical fiber 66 transmits light 68 between monochromator 58 and the collimator lens 74. The output of the adjustable light emitting device is a nominally collimated light beam 76 with user-defined wavelength and spectral width.

The light exiting optical fiber 66 is dispersed as a light pattern 70 along collimator lens assembly 74. This collimator lens assembly 74 serves to generate a nominally collimated light beam 76. The nominally collimated light 76 is desired so that the angle of incidence of the light along surface 81 of the sensor targeted area 114 may be generally well defined.

In one arrangement, the collimator lens assembly 74 is arranged such that a diameter (d) of the collimated beam 76 is large enough to cover a relevant target area of interest on the biosensor 80. In FIG. 2, the area of interest on the biosensor 80 is represented by sensor target area 114. Preferably, the diameter of the light beam 76 may be approximately from about 5 millimeters to about 150 millimeters.

In one arrangement, light source 52 is used to generate a generally wide spectrum of light. Such wide spectrum of light could be white light generated from various types of light sources such as a halogen light source, or a light emitting diode (LED). In one arrangement, the full spectral width as half maximum intensity for light from an LED source can be as wide as from approximately 30 nm to about 50 nm. In an alternative system, an LED with a spectral peak at approximately 880 nm may be used. Such an alternative system could generate light having a spectral range of from approximately 830 nm to approximately 900 nm. Preferably, the available wavelengths of light will be adjusted to generally match the sensor 80 resonance PWV of the sensor target area 114.

As described above, optical fiber 56 is used to transmit light 54 from the light source 52 to an entrance port 62 of monochromator 58. Other types of optical fiber arrangements may also be used. For example, in one alternative arrangement, optical fiber 56 may comprise a multimode fiber. Such a multimode fiber could have a core diameter of approximately 400 micrometers.

Aside from an entrance port 62, the monochromator 58 also has an exit port 64. At exit port 64 of the monochromator 58, the output light 68 preferably has a generally narrow wavelength range or spectral width. This generally narrow spectral width can be defined as one operating parameter of the monochromator 58. During the imaging process, the spectral width of light 76 is adjusted so as to achieve desired spectral resolution for the image. The peak wavelength of light 76 is adjusted by a wavelength adjustment mechanism 60. The adjustment mechanism may be used to adjust a peak wavelength bandwidth. In one preferred arrangement, a spectral width of the output light 76 may typically be within the range of approximately 0.1 nm to about 5 nm.

Adjustable light source 42 may take a variety of forms. For example, in one arrangement, the adjustable light source 42 may comprise a monochromator 58. In such a case, the adjustment mechanism 62 may include a manual micrometer or alternatively, a motorized micrometer. Alternatively, the light collection device 42 may comprise an adjustment mechanism located remotely from the monochromator 58. In such a case, a user located remotely from the adjustable light source 42 may define the wavelength and the spectral width of light beam 76. For example, in one arrangement, a user operating the video image monitoring system 120 may electronically or manually alter the wavelength and the spectral width. In another arrangement, based on viewing an image 127 on the video image monitoring system 120, a user may electronically or manually alter the wavelength and the spectral width.

In yet another arrangement, the monitoring system 120 may comprise software that may be used to vary the wavelength and the spectral width of the monochromator 58. For example, varying the wavelength and the spectral width could be based on certain characteristics of a generated image 127. In an alternative arrangement, the adjustable light source may comprise a tunable laser or a plurality of tunable lasers.

Filtering Mechanism

As further illustrated in FIG. 2, light 68 is transmitted to the filtering mechanism 44. The filtering mechanism 44 is generally used to transmit normally collimated light towards a surface 81 of the biosensor 80. In one arrangement, this filtering mechanism comprises a beam splitter 90 and a polarizer filter 94.

The collimated light beam 76 is incident on beam splitter 90. Beam splitter 90 reflects a certain percentage of the incoming collimated light 76. In one arrangement, beam splitter 90 reflects approximately 50% of the incident light beam 76 and redirects this reflected light beam 77 toward a polarizer filter 94 in the direction of the biosensor 80. Polarizer filter 94 may be used to generate linearly polarized light 98, whereas the light beam 77 may be randomly polarized.

Figure 3:
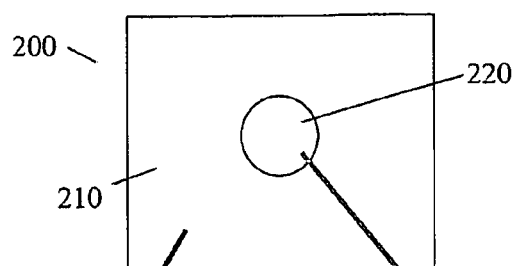
FIGS. 3(a-e) illustrate various diagrams illustrating certain principles of operation of one embodiment of the system illustrated in FIG. 2.
Figure 3B:
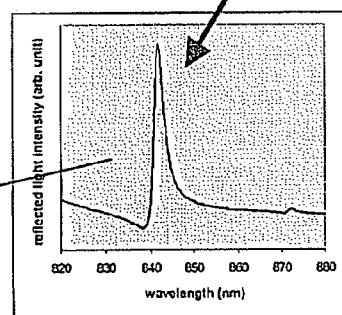
Figure 3D:
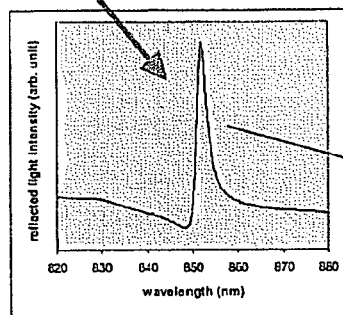
Figure 3C:
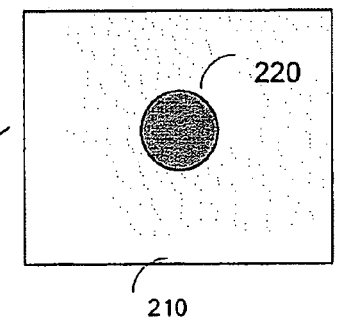
Figure 3E:
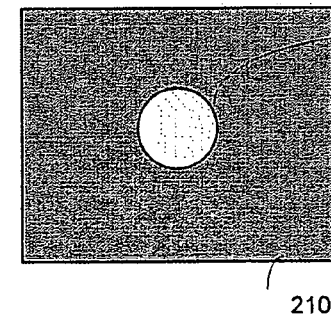

The polarizer filter 94 may be embedded in a larger assembly, not shown in FIG. 3. Embedding such a polarizer filter 94 allows for the rotation of the polarization direction that may be required for detection of the PWV of target area 114 of sensor 80.

Sensor 80 may be a dry type sensor or may be a sensor immersed in liquid. In the arrangement illustrated in FIG. 2, the sensor 80 includes a liquid container 102 that contains a liquid 100. In such an arrangement, the liquid container 102 may be bonded to sensor 80. Liquid 100, provided in liquid container 102, may be an aqueous solution containing various reagents for biomolecular assays. Alternative liquids could also be used, such as water, buffers, or cell growth media. Alternatively, and as discussed in greater detail below, the sensor 80 may be dry type of sensor and may be exposed to air.

Light Collection Device

A linearly polarized light beam 98 is incident on the target area 114 of sensor 80, preferably the polarized light is incident on the surface 81 of biosensor 80 in a nominally perpendicular direction. The light that is reflected by beam splitter 90, reflected light 82, includes the spectral information of the targeted sensor area. This reflected light 82 passes through the beam splitter 90, with preferably about 50% transmission. Reflected light 82 then enters the light collection device 46 where it is preferably first received by a telecentric lens 88. Such telecentric lens 88 may comprise such telecentric lenses generally known in the relevant art such as the MVO Telecentric Lenses offered by Edmund Industrial Optics of Barrington, N.J. <<http://www.edmundoptics.com/US/>>

The light 116 exiting the telecentric lens 88 forms an image 102 of the sensor target area 114. Preferably, the light 116 exiting the telecentric lens 88 forms a sensor target image 102 on a CCD camera 110. The CCD camera image 102 may then be represented as a video image 127 on a video monitor 126 of image-capture system 120. The image capture system could comprise a computing device including a computer, a monitor, and a data input device 124 such as a keyboard and/or mouse. The monitor 126 may be used to view a visual representation 127 of the camera image 102. Based on this visual representation of the image 102, a user may utilize the image capture system 120 to provide further adjustments to the wavelength of light 76 produced by light source device 42. Alternatively, these further adjustments may occur automatically via image processing software installed on the image capture system 120 or remotely, as on a remote server.

To operate system 50, a user views the image 127 and then adjusts the wavelength of light 68 generated by the monochromator 58 accordingly. In one arrangement, the user adjusts the wavelength by way of the adjustment mechanism 60. This adjustment mechanism resides on the monochromator 58 or alternatively this adjustment mechanism resides remotely from the monochromator 58. Preferably, the adjustment mechanism is adjusted so that the wavelength of light 68 exiting the monochromator 58 matches the PWV of the sensor target area 114.

When the wavelength of light 68 matches a PWV of the sensor target area 114, this target area 114 will appear as image 102 as a distinguishing area. For example, when the light 68 matches the PWV of the target area, increased reflectance is obtained and this results in an image having an area that shows up on the image 102 as an illuminated or bright area. Consequently, where there are sensor areas where the PWVs are different from the wavelength of light 68, these areas will not generate a high degree of reflectance and therefore these areas will appear as dark areas. By adjusting the wavelength of light 68 by using the system 50, a user can efficiently and quickly determine PWVs of various target areas on a surface of the sensor 80.

FIGS. 3(*a-e*) depict various diagrams illustrating certain principles of operation of one embodiment of the system 50 illustrated in FIG. 2. In FIG. 3(*a*), a simulated object under investigation 200 is provided. Preferably, such an object comprises a sensor such as the sensor 80 illustrated in FIG. 2. There are two regions of object or sensor 200 that will be investigated. First, there is a rectangular region 210 and secondly there is a circular region 220. Each sensor area 210, 220 will have a biosensor spectral associated with the specific area and will also, therefore, have a respective PWV associated thereto. For example, the first region 210 may comprise a sensor surface having a first reflective peak. The second region 220 may comprise a material bound to the sensor surface such as proteins, cells, or bio-molecules. This second region 220 will then have a second reflective peak having a different wavelength than the first region or different from the first reflective peak.

In this example, and by utilizing the image apparatus illustrated in FIG. 2, a user could vary the wavelength of light 68 by adjusting the wavelength adjustment mechanism from a minimum of approximately 820 nm to a maximum of approximately 880 nm. By varying the wavelength over this range, it could be determined that the first region or the rectangular region 210 would have a first biosensor reflection spectrum 212. This biosensor reflection spectrum 212 is illustrated in FIG. 3(*b*). Then, when the image apparatus illustrated in FIG. 3 is used to alter a new sensor target area, in this example, such target area could be changed to circular region 220, the second region or the circular region 220 would comprise a second biosensor reflection spectrum 222 that is different than the biosensor spectrum 212 of the first region 210.

The biosensor spectral 212 associated with the rectangular region in FIG. 3(*a*) is illustrated in FIG. 3(*b*). FIG. 3(*b*) illustrates a graph of reflected light intensity versus wavelength. As can be seen from this graph, the biosensor spectral 222 associated with the circular region 220 of FIG. 3(*a*) is illustrated in FIG. 3(*d*). As can be seen from FIGS. 3(*b*) and 3(*d*), the biosensor spectral generally graphs the reflected light intensity (in this arrangement, reflected light intensity is provided via arbitrary units) versus wavelength (in this arrangement, wavelength is provided in nm). Comparing FIGS. 3(*b*) and 3(*d*), it can be seen that the regions 210, and 220 have different PWVs. As illustrated in FIG. 3(*b*), the rectangular region 210 has a PWV of approximately 842 nm. And as can be seen from FIG. 3(*d*), the circular region 220 of sensor 200 has a PWV of approximately 852 nm.

Rectangular region 210 appears to have uniform PWV, in this example the uniform PWV is approximately 842 nm as shown by the spectral peak 212. The circular region 220 appears to have a uniform PWV of approximately 852 nm. In one embodiment, the first region 210 may be a sensor substrate without biomolecular adsorption, while the second region 220 may be an area of the sensor with biomolecular adsorption.

Returning to FIG. 2, when system 50 is operated, the wavelength of light 68 is adjusted throughout a predetermined wavelength range. Such a range could be, for example, between 820 nm and 880 nm. With a wavelength of 842 nm, the generated image (See FIG. 2, image 102) may resemble the image shown as image 214 in FIG. 3(*c*). As can be seen from FIG. 3(*c*), region 210 appears brighter than region 220 which appears dark. With a light wavelength of 852 nm, the generated image resembles that shown as 224: region 210 represents a darker image while region 220 represents a brighter image.

The system 50 illustrated in FIG. 2 has many other alternative uses aside from imaging biosensor surfaces and determining if such a surface has contains certain coatings or other biological matter. For example, and as detailed above, the system 50 may also be used to distinguish certain biomolecular adsorptions occurring on a sensor. Another application for the system 50 includes investigating certain inconsistencies and/or defects of the sensor device. Such inconsistencies or defects may occur during sensor fabrication, sensor storage, sensor shipping, or even during sensor usage. For example, system 50 provides an efficient method of determining whether or not a biological coating has been deposited along a biosensor surface according to certain specifications.

Additionally, detection of certain inconsistencies or defects may also be useful for quality control, quality assurance, surface treatment, and/or surface coating processes. For example, FIGS. 4(*a-d*) depicts imaging of surface inconsistencies or defects on a sensor with the system 50. A simulated sensor area under study is indicated as object area or sensor area 300. For example, sensor area 300 could include another targeted area along the surface of the same sensor that was previously imaged in FIGS. 3 (*a-e*). In the example provided in FIG. 4(*a-d*), sensor 300 includes two target areas of investigation: a rectangular region 310 and a defect region 320. The rectangular region 310 and the defect region 320 will have different biosensor spectrum. For example, region 310 may have a biosensor spectrum of 312 illustrated in FIG. 4(*b*) while defect region has a biosensor spectrum 322 illustrated in FIG. 4(*c*). Within the rectangular (i.e., non-defect) region 310, the biosensor spectrum should appear normal. That is, the biosensor spectrum should provide a peak reflectivity of approximately PWV (i.e., at approximately 842 nm) approaching 100%. (See FIG. 4 (*b*)). However, within the defect region 320, the biosensor spectrum appears to be severely reduced. This reduced peak reflectivity of defect region 320 is provided by the reflectance value shown as peek value 322 in Figure (c). During imaging process of the system 50, when the wavelength of light 68 is adjusted to approximately 842 nm, a generated image 314 in FIG. 4(d) is produced. That is, if a light with wavelength of approximately 842 nm is provided along the surface 300, the defect portion 320 of object 300 will not reflect a larger degree of this incoming light and therefore will appear as a dark region 318 as shown in FIG. 4(d). In this case, the defect region 320 shows up as a dark region 318 while the 310 portion of the object will reflect a high degree of the light and appear as a bright image or background 316.

As previously discussed, the wavelength adjustment mechanism 60 may be manual, automatic, or motorized. Alternatively, the adjustment mechanism may be automated through a feedback system. For example, such a feedback system could be based on images acquired by the system 50, to thereby achieve a particular desired imaging configuration. An example configuration is when the total light intensity in the image is maximized, corresponding to an approximate optimization of the biosensor image.

Applications of imaging a subwavelength structured surface biosensor may also include: inspection and quality control during sensor fabrication, spatially resolved biomolecular interaction assays done on subwavelength structured surface biosensors, microarray applications, cell based assay applications, patterned surface biomolecular assay applications, SPR (Surface plasma resonance) imaging, as well as subwavelength structured surface biosensor imaging.

Exemplary embodiments have been described. Those skilled in the art will understand, however, that changes and modifications may be made to these embodiments without departing from the true scope and spirit of the present invention, which is defined by the claims.

What is claimed is:

1. An apparatus for generating a biosensor image, said apparatus comprising:
   a guided mode resonant sensor having a sub-wavelength grating structure;
   a light source;
   an adjustable monochromator optically coupled to said light source, said adjustable monochromator adjusting a spectrum of light from said light source to a define a narrow band of wavelengths that illuminate a surface of a biosensor target area on the sub-wavelength grating structure, said narrow band of wavelengths substantially centered at a target area PWV (peak wavelength value); and
   a telecentric lens for received the narrow band of wavelengths reflected from said surface of said biosensor target area and generating an image of said biosensor target area.

2. The apparatus of claim 1 wherein said light source generates white light.

3. The apparatus of claim 1 wherein said light source comprises an LED.

4. The apparatus of claim 1 wherein said light source comprises a halogen light source.

5. The apparatus of claim 1 wherein said adjustable monochromator comprises a micrometer.

6. The apparatus of claim 5 wherein said micrometer comprises a manual micrometer.

7. The apparatus of claim 1 wherein said light source is optically coupled to said adjustable monochromator by a multimode fiber.

\* \* \* \* \*